United States Patent [19]

Kamei

[11] Patent Number: 5,112,982
[45] Date of Patent: May 12, 1992

[54] PROCESS FOR PREPARING 2,6-DICHLOROPYRIDINE

[75] Inventor: Noboru Kamei, Arai, Japan

[73] Assignee: Daicel Chemical Industries Ltd., Osaka, Japan

[21] Appl. No.: 530,507

[22] Filed: May 31, 1990

Related U.S. Application Data

[63] Continuation of Ser. No. 221,821, Jul. 20, 1988, abandoned.

[30] Foreign Application Priority Data

Jul. 20, 1987 [JP] Japan ................... 62-180714

[51] Int. Cl.$^5$ .................. C07D 213/61; C07D 213/28
[52] U.S. Cl. .................... 546/345; 546/250
[58] Field of Search .......................... 546/345

[56] References Cited

U.S. PATENT DOCUMENTS

| | | | |
|---|---|---|---|
| 3,186,994 | 6/1965 | Johnston et al. | 546/345 |
| 3,251,848 | 5/1966 | Taplin | 546/345 |
| 3,557,124 | 1/1971 | Stringham et al. | 546/345 |
| 4,701,532 | 10/1987 | Humphreys et al. | 546/345 |

*Primary Examiner*—Alan L. Rotman
*Attorney, Agent, or Firm*—Sughrue, Mion, Zinn, Macpeak & Seas

[57] ABSTRACT

A process for preparing 2,6-dichloropyridine, which comprises reacting 2-chloropyridine with chlorine in a liquid phase in the absence of a catalyst at a temperature not lower than 160° C. According to the process, high-purity 2,6-dichloropyridine can be prepared in a high yield with ease.

2 Claims, No Drawings

PROCESS FOR PREPARING 2,6-DICHLOROPYRIDINE

This is a continuation of application Ser. No. 07/221,821 filed Jul. 20, 1988.

FIELD OF THE INVENTION

This invention relates to a process for preparing 2,6-dichloropyridine by starting with 2-chloropyridine or a mixture of 2-chloropyridine and 2,6-dichloropyridine.

BACKGROUND OF THE INVENTION 2,6-Dichloropyridine is useful as a starting material for preparing 2,3,5,6-tetrachloropyridine. 2,3,5,6-Tetrachloropyridine is generally prepared by chlorinating 2,6-dichloropyridine in a liquid phase in the presence of a metal halide as described in U.S. Pat. No. 3,538,100. This process provides 2,3,5,6-tetrachloropyridine at a purity as high as 96% or more without involving any purification procedure. Since the reaction successively proceeds, 2,3,6-trichloropyridine is also produced during the reaction, reaching a purity exceeding 85%. Therefore, this process is also admittedly excellent as a process for producing 2,3,6-trichloropyridine. However, satisfactory achievement of the process requires use of high-purity 2,6-dichloropyridine as a starting material. Impurities, e.g., pyridine and 2-chloropyridine, in the starting 2,6-dichloropyridine would result in disadvantages, such as formation of tar substances as by-products, reduction of product purity, reduction of reaction rate, and the like.

On the other hand, known processes for preparing 2,6-dichloropyridine include (1) a process comprising photo-chlorination of pyridine in a gaseous phase as taught in JP-B-52-3935, JP-B-52-3936, and JP-B-55-4742, and JP-A-60-78967 (the term "JP-B" as used herein means an "examined published Japanese patent application" and "JP-A" as used herein means an "unexamined published Japanese patent application") and (2) a process comprising photo-chlorination of 2-chloropyridine in a liquid phase as taught in U.S. Patent 3,557,124 and JP-B-55-4744.

The process (1) concomitantly produces 2-chloropyridine so that the yield of the desired 2,6-dichloropyridine is not always satisfactory. Besides, purification of the resulting product requires a number of stages including neutralization of the reaction product with an alkali, extraction with a solvent, and fractional distillation of the extract to separate the extracting solvent, pyridine, 2-chloropyridiene, and 2,6-dichloropyridine, thus attaining only a low yield from pyridine. The 2-chloropyridine formed as a by-product in the process (1) may be subjected to the process (2) to effectively obtain 2,6-dichloropyridine, but the process (2) not only needs an apparatus for photo reaction independently of the apparatus for photochlorination of pyridine but also causes additional problems, such as deposition of 2-chloropyridine hydrochloride onto a lamp.

It has hitherto been considered that the chlorination reaction of 2-chloropyridine in a liquid phase would be greatly retarded unless the reaction is carried out under light irradiation or in the presence of a catalyst. This is believed to arise from the fact that, with no catalyst being used, the liquid phase reaction has actually been conducted at a temperature lower than 160° C and at atmospheric pressure because 2-chloropyridine has a boiling point of 170° C. Under such reaction conditions, the reaction is slow and is also accompanied by formation of large quantities of by-products, e.g., 2,3-dichloropyridine and 2,5-dichloropyridine. In addition, the reaction concomitantly produces products of higher chlorination order, e.g., 2,3,5-trichloropyridine, 2,3,5,6-tetrachloropyridine, and pentachloropyridine.

On the other hand, in cases where the reaction is effected in the presence of a metal halide as a catalyst, the reaction is accelerated but still involves problems of formation, as a - by-product, of 2,3-dichloropyridine or 2,5-dichloropyridine and formation of chlorination products of higher order which is considered to accompany such side reactions.

SUMMARY OF THE INVENTION

Accordingly, one object of this invention is to overcome the above-described problems concerning the production of 2,6-dichloropyridine and to provide a process for preparing high-purity 2,6-dichloropyridine in a high yield.

In the light of the stated circumstances, the inventor has conducted extensive investigations on a process for selectively and easily preparing 2,6-dichloropyridine in a liquid phase in a higher yield as compared with the conventional processes. As a result, it has been unexpectedly found that 2,6-dichloropyridine can be obtained from 2-chloropyridine with a high selectivity when the chlorination reaction is carried out at a temperature not lower than 160° C., preferably not lower than 180° C., with no catalyst being present. The present invention has been completed based on this finding.

The present invention relates to a process for preparing 2,6-dichloropyridine which comprises reacting 2-chloropyridine with chlorine in a liquid phase in the absence of a catalyst at a temperature not lower than 160° C.

DETAILED DESCRIPTION OF THE INVENTION

The starting material may be either 2-chloropyridine alone or a mixture of 2-chloropyridine and 2,6-dichloropyridine. The 2,6-dichloropyridine present in the starting material does not undergo reaction at all under the above-specified conditions similarly to the produced 2,6-dichloropyridine. Therefore, a mixture of 2-chloropyridine and 2,6-dichloropyridine, which is obtained by, for example, photo-chlorination of pyridine, can be utilized as a starting material. In this case, the present invention eventually provides an efficient process for obtaining 2,6-dichloropyridine from pyridine.

Since chlorine absorption in the reaction system varies depending on the form or shape of a reaction vessel to be employed, the amount of chlorine to be charged is appropriately determined by measuring a chlorine concentration in the exhaust gas. As a general rule, the chlorine absorption increases with a rise of temperature or pressure or a rise of 2-chloropyridine concentration.

The reaction temperature should be at least 160° C. to ensure the reaction rate, selectivity, etc. and is preferably at least 180° C.

The rise of reaction temperature requires a rise of reaction pressure or the like operation as hereinafter described. In view of the ease of operation, the reaction is usually performed at a temperature below 250° C.

If the reaction is effected at a temperature near the boiling point of the reaction system, that is, at reflux, absorption of chlorine would be suppressed to seriously retard the reaction. Therefore, the reaction temperature is desirably lower than the boiling point of the reaction mixture by at least 10° C. Hence, in order to carry out the reaction at a preferred temperature, i.e., 180° C. or higher, the boiling point of the reaction mixture can be increased, for example, by raising the inner pressure of the reactor or using a mixture with 2,6-dichloropyridine as a starting material.

In the process of this invention, a reaction solvent or the like is not particularly necessary, but a solvent which serves to increase the boiling point of the reaction mixture without participating in the reaction may be used. For instance, 2,6-dichloropyridine that is a desired product, 2,3,6-trichloropyridine, 2,3,5,6-tetrachloropyridine, etc. can be used for this effect.

As described above, the process of this invention requires neither light nor a catalyst and produces 2,6-dichloropyridine from 2-chloropyridine or its mixture with 2,6-dichloropyridine more easily and in a higher yield as compared with the conventional processes. According to this process, the reaction shows high selectivity without forming black impurities as does in the case of using a catalyst.

The present invention is of particularly high industrial value in the point that a mixed liquid of 2-chloropyridine and 2,6-dichloropyridine obtained through gaseous phase photo-chlorination of pyridine can be utilized as a starting material for producing high-purity 2,6-dichloropyridine. In other words, the present invention provides a well established process for preparing 2,6-dichloropyridine in an excellent overall yield based on the starting pyridine.

The 2,6-dichloropyridine obtained by the present invention can be used as it is as a starting material for preparing 2,3,6-trichloropyridine or 2,3,5,6-tetrachloropyridine without requiring any purification procedure. Thus, the present invention has also established a process for preparing 2,3,6-trichloropyridine or 2,3,5,6-tetrachloropyridine, starting with pyridine.

The present invention is now illustrated in greater detail with reference to the following Examples, Comparative Examples, and Reference Example, but it should be understood that the present invention is not deemed to be limited thereto. In these examples, all the percents are by weight unless otherwise indicated.

EXAMPLE 1

In a separable flask equipped with a stirrer were charged 175 g of 2-chloropyridine and 288 g of 2,6-dichloropyridine, and chlorine was bubbled therethrough at a rate of 2 l/hr while keepting the mixture at 180° C. Fifty hours later, the reaction mixture was found to contain 0.8% of 2-chloropyridine, 97.5% of 2,6-dichloropyridine and, as impurities, 1.1% of 2,3,6-trichloropyridine and 0.4% of 2,3,5,6-tetrachloropyridine. The reaction mixture assumed pale yellow, proving substantial absence of a tar substance.

EXAMPLE 2

In a pressure-resistant glass-made reactor equipped with a stirrer was charged 350 g of 2-chloropyridine, and chlorine was bubbled therethrough at a rate of 5 l/hr while keeping the reaction mixture at a temperature between 195° C. and 200° C. under a pressure of 1 kg/cm$^2$G. Fourty hours later, the reaction mixture was found to contain 0.5% of 2-chloropyridine, 98.5% of 2,6-dichloropyridine and, as impurities, 0.8% of 2,3,6-trichloropyridine and 0.5% of 2,3,5,6-tetrachloropyridine. The reaction mixture assumed pale yellow, proving substantial absence of a tar substance.

COMPARATIVE EXAMPLE 1

The procedure of Example 2 was repeated, with the exception that the reaction was carried out at 150° C. and at atmospheric pressure. After about 130 hours, the 2-chloropyridine concentration of the reaction mixture was found to be 1.1%. At this point, the reaction mixture contained 84% of 2,6-dichloropyridine and, as impurities, 4% of 2,3-dichloropyridine, 5% of 2,3,5-trichloropyridine, 5% of 2,3,5,6-tetrachloropyridine, and 1% of pentachloropyridine.

COMPARATIVE EXAMPLE 2

The procedure of Example 1 was repeated, with the exception that the reaction system further contained 25 g of ferric chloride. About 55 hours later, the 2-chloropyridine concentration decreased to 2.3%. At this point, the reaction mixture was found to contain 81% of 2,6-dichloropyridine and, in addition, 5% of 2,3- and 2,5-dichloropyridines, 3% of 2,3,5-trichloropyridine, 4% of 2,3,6-trichloropyridine, 3% of 2,3,5,6-tetrachloropyridine, and 2% of pentachloropyridine.

REFERENCE EXAMPLE

To the reaction mixture containing 2,6-dichloropyridine as obtained in Example 2 was added 25 g of ferric chloride, and chlorine was introduced therein at a rate of 5 l/hr while maintaining the mixture at a temperature of 180° C. Fifteen hours later, gas chromatography revealed that the reaction mixture contained 88% of 2,3,6-trichloropyridine. After the chlorine introduction for 38 hours in total, there was obtained a mixture containing 97.5% of 2,3,5,6-tetrachloropyridine with, as impurities, 0.7% of the unreacted 2,3,6-trichloropyridine, 1,6% of pentachloropyridine, and 0.2% of 2,3,5-trichloropyridine.

While the invention has been described in detail and with reference to specific embodiments thereof, it will be apparent to one skilled in the art that various changes and modifications can be made therein without departing from the spirit and scope thereof.

What is claimed is:

1. A process for preparing 2,6-dichloropyridine, which comprises reacting 2-chloropyridine with chlorine in a liquid phase in the absence of a catalyst and in the absence of light at a temperature between 195° C. and 200° C. and at elevated pressure.

2. A process as claimed in claim 1, wherein said 2-chloropyridine is in the form of a mixture with 2,6-dichloropyridine.

* * * * *